US005703013A

United States Patent [19]
Caulder et al.

[11] Patent Number: 5,703,013
[45] Date of Patent: Dec. 30, 1997

[54] PROCESS AND COMPOSITION FOR CONTROLLING WEEDS

[75] Inventors: Jerry Caulder, San Diego; R. Hugh Crowley, Oceanside; Paul S. Zorner, La Costa; Steven L. Evans, San Diego, all of Calif.

[73] Assignee: Mycogen Corporation, San Diego, Calif.

[21] Appl. No.: 468,601

[22] Filed: Jun. 7, 1995

Related U.S. Application Data

[62] Division of Ser. No. 396,372, Feb. 28, 1995, abandoned, which is a continuation of Ser. No. 229,866, Apr. 19, 1994, abandoned, which is a continuation of Ser. No. 980,015, Nov. 23, 1992, abandoned, which is a division of Ser. No. 638,708, Jan. 19, 1991, Pat. No. 5,196,044.

[51] Int. Cl.$^6$ .................................................. A01N 43/88
[52] U.S. Cl. ........................................ 504/131; 504/142
[58] Field of Search ............................ 504/142, 136, 504/131

[56] References Cited

U.S. PATENT DOCUMENTS

| | | | |
|---|---|---|---|
| 2,622,975 | 12/1952 | Zimmerman et al. | 504/147 |
| 3,799,758 | 3/1974 | Franz | 504/206 |
| 4,134,754 | 1/1979 | Hoffmann | 504/110 |
| 4,638,068 | 1/1987 | Los | 504/191 |
| 4,975,110 | 12/1990 | Puritch et al. | 504/142 |
| 5,035,741 | 7/1991 | Puritch et al. | 504/142 |
| 5,196,044 | 3/1993 | Caulder et al. | 504/127 |

FOREIGN PATENT DOCUMENTS

| | | |
|---|---|---|
| 0115622 | 8/1984 | European Pat. Off. |
| 8903178 | 4/1989 | WIPO |
| 9207467 | 5/1992 | WIPO |

OTHER PUBLICATIONS

The Agrochemicals Handbook, 3rd Edition, Hartley et al editors; The Royal Society of Chemistry, Nottingham, England, 1991, PA0034.
Japanese Patent No. 59 193 809 issued Apr. 19, 1983 (abstract).
Japanese Patent No. 61 106 501 issued Oct. 30, 1984 (abstract).
Japanese Patent No. 61 289 004 issued Jun. 18, 1985 (abstract).
The Agrochemicals Handbook (1987) 2nd Edition, Hartley and Kidd editors; The Royal Society of Chemistry, Nottingham, England, pp. A045 and A138.
Turner, D.J. (1985) "Effects on glyphosphate performance of formulation, additives and mixing with other herbicides" The Herbicide Glyphosate, Grossbard and Atkinson, editors, pp. 221–240.
Japanese Patent No. 59 193 804 issued Nov. 2, 1984 (abstract).
Japanese Patent No. 59 199 608 issued Apr. 27, 1983 (abstract).
Japanese Patent No. 59 199 609 issued Apr. 28, 1983 (abstract).

Primary Examiner—José G. Dees
Assistant Examiner—Brian G. Bembenick
Attorney, Agent, or Firm—Saliwanchik, Lloyd & Saliwanchik

[57] ABSTRACT

Described and claimed are methods and compositions for the control of unwanted vegetation. According to the subject invention, a fatty acid or mixture of fatty acids can be combined with one or more chemical herbicides to achieve synergistic control of a broad range of plants.

17 Claims, No Drawings

PROCESS AND COMPOSITION FOR CONTROLLING WEEDS

This application is a divisional of U.S. Ser. No. 08/396,372, filed Mar. 28, 1995 (abandoned), which is a continuation of U.S. Ser. No. 08/229,866, filed Apr. 19, 1994 (abandoned), which is a continuation of U.S. Ser. No. 07/980,015, filed Nov. 23, 1992 (abandoned), which is a divisional of U.S. Ser. No. 07/638,708, filed Jan. 8, 1991 (U.S. Pat. No. 5,196,044).

BACKGROUND OF THE INVENTION

Weeds cost farmers billions of dollars annually in crop losses and in the expense of keeping weeds under control. Much of the cost of intertillage of row crops, maintenance of fallow, seedbed preparation, and seed cleaning is chargeable to weed control. Suppression of weeds along highways and railroad right-of-ways, and in irrigation ditches, navigation channels, yards, parks, grounds, and home gardens also is expensive. Ragweed pollen is the source of annual periodic distress to several million hayfever sufferers. Poison ivy, poison oak, poison sumac, nettles, thistles, sandburs, and puncturevine also bring pain to millions. Weeds also serve as hosts for other crop diseases as well as for insect pests.

The losses caused by weeds in agricultural production environments include decrease in crop yield, reduced crop quality, increased irrigation costs, increased harvesting costs, decreased land value, injury to livestock, and crop damage from insects and diseases harbored by the weeds.

Chemical herbicides have provided an effective method of weed control; however, the public has become concerned about the amount of residual chemicals which might be found in food, ground water, and the environment. Stringent new restrictions on the use of herbicides and the elimination of some effective herbicides from the market place could limit economical and effective options for controlling costly weeds. Additionally, the visually apparent phytotoxic effects of some systemic herbicides appear very slowly on the target weeds, so pesticide users often seek methods by which the apparent speed of action of the herbicide is increased.

There is a great need for novel weed control methods which reduce the amount of chemical herbicide necessary to obtain acceptable levels of weed control. Researchers have experimented with various combinations of chemicals as one approach to identify compositions which have desirable herbicidal characteristics. In the rare instance, unexpected activity of the combination of chemicals is obtained. For example, selective control of annual weeds with a composition of fatty acids mixed with ethylmaleimide, colchicine, 2,4-dinitrohalobenzene, or 2,4-dinitrophenol has been described in the Japanese patent abstract JP61106501. It should be noted that the compounds which were mixed with the fatty acids are not known for their agricultural use and, in fact, may be inappropriate for many herbicidal applications. Other abstracts disclosing a variety of fatty acid derivatives with various chemical compounds include JP59199608 (halogen or cyano derivatives of fatty acids with 2-amino 1,2,4-triazole), JP59199609 (halogen or cyano derivative of fatty acid with 3-amino 1,2,4-triazole), and JP59193804 (acetylenic derivative). Unlike the abstracts mentioned above, the current invention pertains to certain combinations of fatty acids and chemical herbicides which can provide broad range or selective herbicidal activity.

BRIEF SUMMARY OF THE INVENTION

This invention concerns novel compositions and methods for selective or non-selective control of plants. We have discovered that application to weeds of a combination of certain chemical herbicides and one or more substituted (or unsubstituted) saturated (or unsaturated) fatty acids (or their salts) results in the effective control of a broad range of plants. The fatty acids of the subject invention can be from about C7 to about C20 and can be, for example, in the epoxide, cyclopropane, methylated, or hydroxylated forms. The fatty acids of the subject invention can be represented by the following formula:

wherein $R_1$=C6 to C19 saturated or unsaturated hydrocarbon, or an epoxide, or cyclopropane thereof $Y_1$=H, C1–C5 hydrocarbon, or hydroxyl at any position along $R_1$ $Y_2$=H, C1–C5 hydrocarbon, or hydroxyl at any position along $R_1$ $R_2$=H, or salt.

Specifically exemplified herein are saturated fatty acids of length C7 to C11 in combination with chemical herbicides. The use of the compositions described here, when used in the proportions and application rates set forth more fully hereinafter, results in an unexpected, enhanced herbicidal effect.

The herbicides used according to the subject invention can be systemic herbicides. In one preferred embodiment of the invention, the herbicides may be systemic herbicides with slow uptake rates. The herbicides may or may not be selective. Therefore, using the compositions and procedures of the subject invention, it is possible to achieve enhanced selective control of weeds or enhanced broad range control.

The composition of the present invention comprises a mixture of components wherein said mixture is sufficiently active so that application of the composition enables utilization of reduced amounts of each of the active ingredients while still providing effective weed control. Additionally, application of the prescribed combination of fatty acids and a systemic chemical herbicide often reduces the time required for systemic phytotoxic symptoms to appear on the target weed.

Since the level of weed control obtained following application of the prescribed mixture is generally much superior to that obtained following application of either active component alone, the practice of the present invention provides a desirable economic advantage to the user. Furthermore, the reduction in the amount of chemicals introduced into the environment is an additional advantageous element of the subject invention. Advantageously, the compositions of the subject invention can provide broad range non-selective herbicidal activity. The compositions of the subject invention may also be used to obtain selective control of weeds.

DETAILED DESCRIPTION OF THE INVENTION

The fatty acids used according to the subject invention can be unsubstituted, or substituted, saturated, or unsaturated, fatty acids (or their salts), of about C7 to about C20. Specifically exemplified are fatty acids of length C7 to C11, as typified by, but not limited to, decanoic acid or nonanoic acid. The fatty acid component of the subject invention may be a single fatty acid or a mixture of two or more fatty acids.

A variety of different chemical herbicides can be used alone or in combination according to the subject invention.

The specie herbicides which should be used for a given application can be readily ascertained by a person skilled in the art. Following is a list of herbicides which may be used according to the subject invention.

| HERBICIDE | EXAMPLE |
| --- | --- |
| 1. Phenoxy acids (acids, esters, salts) | 2,4-D, MCPA, Dichlorprop |
| 2. Benzoic acid | Dicamba |
| 3. Aryloxy phenoxypropionate (acids, Flurazifop, Dichlofop esters, salts) | |
| 4. Sulfonyl ureas (acdis, esters) | Chlorimuron, Bensulfuron |
| 5. Imidazilinones | Imazethapyr |
| 6. Bipyridillium | Paraquat |
| 7. Diphenyl ether (acids, salts) | Acifluorfen, Fomesafen |
| 8. Cyclohexanedione | Sethdoxydim, Cycloxydim, Clethodim |
| 9. Methane arsonate | MSMA (Methylarsonic acid) |
| 10. Triazine | Atrazine, Cyanazine |
| 11. Aliphatic carboxylic acids | Dalapon |
| 12. Benzonitrile | Bromoxynil |
| 13. Carbamate | Barban |
| 14. Thiocarbamate | Benthiocarb, Triallate |

Herbicides other than those which are specifically listed above may also be used according to the subject invention. In one preferred embodiment of this invention, a fatty acid is combined with one or more systemic foliar herbicides with slow uptake characteristics. Specifically, the compositions of the subject invention may advantageously comprise a herbicide from one of the following families: phenoxy acids, aryloxy phenoxypropionates, cyclohexanediones, sulfonyl ureas, and imidazilinones. Of these families, imidazilinones and sulfonyl ureas are particularly advantageous. A further preferred embodiment is the use of a fatty acid with glyphosate. This combination has shown substantial synergy as described in the examples below.

Specific examples of the chemical herbicides which can be used together with the fatty acid in the composition of the subject invention include, but are not limited to, glyphosate (N-[phosphonomethyl]glycine, isopropylamine salt), imazapyr ([±],-2-[4,5-dihydro-4-methyl-4-[1-methylethyl]-5-oxo-1H-imidazol-2-yl]-3-pyridinecarboxylic acid), sethoxydim (2-[1-[ethoxyimino]butyl]-5-[2-[ethyl-thio]propyl]-3-hydroxy-2-cyclohexen-1-one), or paraquat (1,1'-dimethyl-4,4'-bipyridinium dichloride), used alone or optionally with agricultural adjuvants with which the herbicides are normally admixed.

One embodiment of the present invention consists of the application of a tankmix of a fatty acid and chemical herbicide. A further embodiment contemplates sequential application of a fatty acid and a chemical herbicide. The process of the subject invention is illustrated in the examples which follow. These examples demonstrate the enhanced synergistic effects achieved through the use of sub-herbicidally effective application rates of the herbicide glyphosate in combination with the fatty acid, nonanoic acid.

Following are examples which illustrate procedures, including the best mode, for practicing the invention. These examples should not be construed as limiting. All percentages are by weight and all solvent mixture proportions are by volume unless otherwise noted.

| PYRAZON | GLYPHOSATE | PICHLORAM | METRIBUZIN |
| --- | --- | --- | --- |
| GLUFOSINATE | CLOPYRALID | BENTAZON | DESMEDIPHAM |
| QUINCLORAC | AMITROLE | PHENMEDIPHAM | |
| TRICLOPYRETHIOZIN | | | |

EXAMPLE 1

A greenhouse trial was carried out to demonstrate the enhanced herbicidal activity obtained following application of a combination of a fatty acid and a chemical herbicide. Purple nutsedge was planted in 4 inch pots in soft-less potting mix (PROMIX) and were cultivated in greenhouses that were maintained at daytime temperatures of 70°–90° F., and which were watered by sub-irrigation every other day, until the plants attained the 8 true leaf stage.

The fatty acid herbicide, nonanoic acid, was prepared by diluting the requisite amount of SHARPSHOOTER 80% formulation with sufficient water to provide spray mixes which, when applied by a track sprayer at an application rate of 25 gallons per acre (gpa) would deliver the field equivalent of, respectively, 0.024, 0.488, 0.976, and 1.952 pounds per acre (lb/acre) of the active ingredient. The herbicide glyphosate, was prepared by diluting the requisite amount of commercial ROUNDUP 4L formulation with sufficient water to provide a spray mix which, when applied at an application rate of 25 gpa by a track sprayer, would deliver the field equivalent of 1.0 (lb/acre) of the active isopropyl amine salt. Additional spray mixes were made up accordingly containing the respective fatty acid in descending order of concentration as set forth above, thus providing a series of dilutions of compositions containing both types of active ingredients in combination.

Purple nutsedge plants were treated with the afore-described spray mixes and appropriate untreated checks in treatment groups consisting of 12 plants each, with a total of 4 replications of a treatment within the test. Following application of the spray mixes at a rate of 25 gpa, the plants were removed to the greenhouse and maintained under good growing conditions for the duration of the test period.

Herbicidal effects were assessed at the indicated days after treatment (DAT) over a time period of 6–27 DAT. The weed control ratings ascertained the extent of control, i.e. reduction in growth, obtained and scored on the basis of 0 to 100 where 100 represents kill of the plants and 0 represents no reduction in growth, as compared to the untreated check. The individual ratings on the four treatment replications were averaged to obtain the average percent control for each particular treatment.

The results of these tests, indicating evaluations at 6, 14 and 27 DAT are indicated in Table 1. Also shown in Table I is the extent of control expected by a combination of herbicides, as based on their respective activities individually. This expected level of control was calculated according to the well known equation:

$$\text{Expectedcontrol} = X + Y - \frac{X*Y}{100}$$

where X=% control by the fatty acid alone and Y=% control by the glyphosate alone (Colby, S. R. (1966) "Calculating synergistic and antagonistic responses of herbicide combinations," Weeds 15:20–22).

TABLE 1

Control of 8 Leaf Nutsedge in a Greenhouse Trial
Days after treatment

| | | | 6 | | | 14 | | | 27 | | |
| --- | --- | --- | --- | --- | --- | --- | --- | --- | --- | --- | --- |
| Nonanoic lb/acre | Glyphosate lb/acre | Approx. wt. ratio, Nonanoic acid to Glyphosate | Expected Control % | Actual Control % | Percent Increase over Expected Control | Expected Control % | Actual Control % | Percent Increase over Expected Control | Expected Control % | Actual Control % | Percent Increase over Expected Control |
| 0.244 | — | — | — | 0 | — | — | 0 | — | — | 0 | — |
| 0.488 | — | — | — | 0 | — | — | 0 | — | — | 0 | — |
| 0.976 | — | — | — | 0 | — | — | 0 | — | — | 5 | — |
| 1.952 | — | — | — | 0 | — | — | 4 | — | — | 8 | — |
| — | 1.0 | — | — | 25 | — | — | 83 | — | — | 82 | — |
| 0.244 | 1.0 | 0.244:1 | 25 | 64 | 156 | 83 | 88 | 6 | 82 | 100 | 22 |
| 0.488 | 1.0 | 0.488:1 | 25 | 56 | 124 | 83 | 93 | 12 | 82 | 100 | 22 |
| 0.976 | 1.0 | 0.976:1 | 25 | 55 | 120 | 83 | 91 | 10 | 83 | 100 | 21 |
| 1.952 | 1.0 | 1.952:1 | 25 | 74 | 196 | 84 | 96 | 15 | 83 | 100 | 20 |

EXAMPLE 2

Additional greenhouse tests were performed to evaluate mixtures of fatty acids and herbicides on mature weeds and at reduced herbicidal rates. Purple nutsedge was grown as described in Example 1 except that it was allowed to reach the 11 leaf stage. Spray mixes of SHARPSHOOTER 80% were prepared to the same concentrations and by the same methods as described in Example 1. Spray mixes of ROUNDUP 4L were prepared by the methods described above, but at such a concentration that, when sprayed at an application rate of 25 gpa by a track sprayer, they would deliver the field equivalent of 0.5 (lb/acre) of the active isopropyl amine salt. Additional spray mixes were made up accordingly containing the respective fatty acid in descending order of concentration as set forth above together with glyphosate at the concentration set forth above, thus providing a series of dilutions of compositions containing both types of active ingredients in combination.

Purple nutsedge plants were treated with the aforedescribed spray mixes and appropriate untreated checks in treatment groups consisting of 12 plants each, with a total of 3 replications of a treatment within the test. Following application of the spray mixes at a rate of 25 gpa, the plants were removed to the greenhouse and maintained under good growing conditions for the duration of the test period.

Herbicidal effects were assessed as percent control in the manner described above at 21 and 56 DAT. The individual ratings on the three treatment replications were averaged to obtain the average percent control for each particular treatment.

The results of these tests are indicated in Table 2. Also shown in Table 2 is the extent of control expected by a combination of herbicides, as calculated in the manner described above.

TABLE 2

Control of 11 Leaf Nutsedge in a Greenhouse Trial
Days after treatment

| | | | 21 | | | 56 | | |
| --- | --- | --- | --- | --- | --- | --- | --- | --- |
| Nonanoic acid lb/ac | Glyphosate lb/ac | Approx. wt. ratio, Nonanoic acid to Glyphosate | Expected Control % | Actual Control % | Percent Increase over Control % | Expected Control % | Actual Control % | Percent Increase over Control % |
| 0.244 | — | — | — | 0 | — | — | 9 | — |
| 0.488 | — | — | — | 0 | — | — | 10 | — |
| 0.976 | — | — | — | 1 | — | — | 13 | — |
| 1.952 | — | — | — | 3 | — | — | 9 | — |
| — | 0.5 | — | — | 38 | — | — | 85 | — |
| 0.244 | 0.5 | 0.488:1 | 39 | 71 | 83 | 86 | 100 | 16 |
| 0.488 | 0.5 | 0.976:1 | 38 | 76 | 100 | 87 | 96 | 11 |
| 0.976 | 0.5 | 1.952:1 | 39 | 73 | 89 | 87 | 98 | 13 |
| 1.952 | 0.5 | 3.904:1 | 40 | 60 | 51 | 86 | 90 | 4 |

EXAMPLE 3

A series of field tests were performed to show the effect of fatty acids in combination with chemical herbicides on mature purple nutsedge and sicklepod. Purple nutsedge and sicklepod were grown to the 8 leaf and 6 leaf stage, respectively, in field plots approximately 16.5 square feet in area. Spray mixes of the fatty acid herbicide, nonanoic acid, was prepared by diluting the requisite amount of SHARPSHOOTER 80% formulation with sufficient water to provide spray mixes which, when applied by a gas-pressurized backpack sprayer at an application rate of 10 gallons per acre (gpa) would deliver to the field 0.975, 1.950 and 2.925 pounds per acre (lb/acre) of the active ingredient. The herbicide glyphosate was prepared by diluting the requisite amount of commercial RODEO (5.4L) formulation with sufficient water to provide a spray mix which, when applied at an application rate of 10 gpa, would deliver to the field 0.5, 1.0 and 1.5 lb/acre of the active isopropyl amine salt. To all glyphosate spray mixes was admixed the surfactant X-77 (Union Carbide) at a final concentration of 0.25% (v/v) in the solutions, as recommended by the manufacturer. Additional spray mixes were made up accordingly containing the respective fatty acid in descending order of concentration as set forth above, thus providing a series of dilutions of compositions containing both types of active ingredients in combination.

The spray mixes, and appropriate checks, were applied to the field plots in a randomized complete block design with 3 replications per treatment. The plants received overhead irrigation every other day during the duration of the experiment. The herbicidal effect of the spray mixes on purple nutsedge, measured as described in Example 1 above, including the expected control of the combinations, 17 DAT are recorded in Table 3. Also recorded are the effects on sicklepod 10 DAT.

SHOOTER 80% formulation with sufficient water to provide spray mixes which, when applied by a pressurized backpack sprayer at an application rate of 25 gpa would deliver to the field 1.95 lb/acre of the active ingredient. The herbicide glyphosate was prepared by diluting the requisite amount of commercial RODEO (5.4L) formulation with sufficient water to provide a spray mix which, when applied at an application rate of 25 gpa, would deliver to the field 0.169, 0.338 and 0.675 lb/acre of the active isopropyl amine salt. Additional spray mixes were made up accordingly containing the glyphosate in descending order of concentration as set forth above together with nonanoic acid at the concentration set forth above, thus providing a series of dilutions of compositions containing both types of active ingredients in combination.

The spray solutions were applied to a field plot approximately 16.5 square feet in area; there were 2 replications per

TABLE 3

Control of Nutsedge and Sicklepod in a Field Trial

| | | | 8 Leaf Nutsedge 17 days after treatment | | | 6 Leaf Sicklepod 10 Days after treatment | | |
|---|---|---|---|---|---|---|---|---|
| Nonanoic acid lb/ac | Glyphosate lb/ac | Approx. wt. ratio, Nonanoic acid to Glyphosate | Expected Control % | Actual Control % | Percent Increase over Control % | Expected Control % | Actual Control % | Percent Increase over Control % |
| 0.975 | — | — | — | 0 | — | — | 0 | — |
| 1.950 | — | — | — | 0 | — | — | 3 | — |
| 2.925 | — | — | — | 0 | — | — | 5 | — |
| — | 0.5 | — | — | 57 | — | — | 23 | — |
| — | 1.0 | — | — | 70 | — | — | 37 | — |
| — | 1.5 | — | — | 77 | — | — | 40 | — |
| 0.975 | 0.5 | 1.95:1 | 57 | 67 | 18 | 23 | 37 | 85 |
| 0.975 | 1.0 | 0.975:1 | 70 | 85 | 21 | 37 | 77 | 108 |
| 0.975 | 1.5 | 0.65:1 | 77 | 85 | 10 | 40 | 93 | 151 |
| 1.950 | 0.5 | 3.9:1 | 57 | 67 | 18 | 37 | 27 | 21 |
| 1.950 | 1.0 | 1.95:1 | 70 | 85 | 21 | 39 | 77 | 98 |
| 1.950 | 1.5 | 1.3:1 | 77 | 88 | 14 | 40 | 98 | 152 |
| 2.925 | 0.5 | 5.85:1 | 57 | 57 | 0 | 40 | 33 | neg. |
| 2.925 | 1.0 | 2.925:1 | 70 | 87 | 24 | 42 | 83 | 98 |
| 2.925 | 1.5 | 1.95:1 | 77 | 83 | 8 | 43 | 98 | 128 |

EXAMPLE 4

The effect of a combination of nonanoic acid and glyphosate on 5 species of plants grown under field conditions was determined. The five plant species, and their growth stage at the time of treatment, were: velvetleaf (3 leaf), corn (4 leaf), barnyardgrass (4 leaf), sicklepod (3 leaf), and nutsedge (2–3 leaf). Spray mixes of nonanoic acid were prepared by diluting the requisite amount of SHARPtreatment. Herbicidal effect was assessed as described in Example 1. The results on purple nutsedge and sicklepod at 14 and 28 DAT are tabulated in Tables 4 and 5, respectively, along with expected values of the combinations calculated according to the method described in Example 1. The results on velvetleaf, corn and barnyardgrass at one rate of the combination are tabulated in Table 6.

TABLE 4

Control of Nutsedge in a Field Trial

| | | | 14 days after treatment | | | 28 Days after treatment | | |
|---|---|---|---|---|---|---|---|---|
| Glyphosate lb/ac | Nonanoic acid lb/ac | Approx. wt. ratio, Nonanoic acid to Glyphosate | Expected Control % | Actual Control % | Percent Increase over Control % | Expected Control % | Actual Control % | Percent Increase over Control % |
| 0.169 | — | — | — | 0 | — | — | 0 | — |
| 0.338 | — | — | — | 13 | — | — | 0 | — |
| 0.675 | — | — | — | 28 | — | — | 0 | — |
| — | 1.95 | — | — | 0 | — | 0 | 0 | — |
| 0.169 | 1.95 | 0.087:1 | 0 | 20 | ∞ | 0 | 35 | ∞ |
| 0.338 | 1.95 | 0.173:1 | 13 | 33 | 154 | 0 | 45 | ∞ |
| 0.675 | 1.95 | 0.346:1 | 28 | 50 | 79 | 0 | 70 | ∞ |

TABLE 5

Control of Sicklepod in a Field Trial

| Glyphosate lb/ac | Nonanoic acid lb/ac | Approx. wt. ratio, Nonanoic acid to Glyphosate | 14 days after treatment | | | 28 Days after treatment | | |
|---|---|---|---|---|---|---|---|---|
| | | | Expected Control % | Actual Control % | Percent Increase over Control % | Expected Control % | Actual Control % | Percent Increase over Control % |
| 0.169 | — | — | — | 0 | — | — | 5 | — |
| 0.338 | — | — | — | 13 | — | — | 12 | — |
| 0.675 | — | — | — | 18 | — | — | 15 | — |
| — | 1.95 | — | — | 10 | — | — | 10 | — |
| 0.169 | 1.95 | 0.087:1 | 10 | 30 | 200 | 15 | 30 | 107 |
| 0.338 | 1.95 | 0.173:1 | 22 | 30 | 38 | 21 | 45 | 116 |
| 0.675 | 1.95 | 0.346:1 | 26 | 45 | 72 | 24 | 55 | 134 |

TABLE 6

Control of Velvetleaf, Corn & Barnyardgrass in a Field Trial
14 Days after treatment

| Glyphosate lb/ac | Nonanoic acid lb/ac | Approx. wt. ratio, Nonanoic acid to Glyphosate | Velvetleaf | | | Corn | | | Barnyardgrass | | |
|---|---|---|---|---|---|---|---|---|---|---|---|
| | | | Expected Control % | Actual Control % | Percent Increase over Expected Control | Expected Control % | Actual Control % | Percent Increase over Expected Control | Expected Control % | Actual Control % | Percent Increase over Expected Control |
| 0.169 | — | — | — | 3 | — | — | 10 | — | — | 13 | — |
| — | 1.95 | — | — | 20 | — | — | 25 | — | — | 18 | — |
| 0.169 | 1.95 | 0.087:1 | 22 | 85 | 279 | 33 | 80 | 146 | 29 | 70 | 144 |

EXAMPLE 5

A field study examined the effect of application of a mixture of nonanoic acid and glyphosate on control of common oats. Common oats were grown to the 5 leaf stage in field plots of approximately 80 square feet area. Nonanoic acid was prepared in a similar manner as described above to yield spray mixes that would deliver to the field, when applied at a rate of 20 gpa, 0.975, 1.95 and 3.9 lb/acre of the active ingredient. Glyphosate was prepared by diluting the requisite amount of the LAWN AND GARDEN (1.6L) formulation with water to obtain a spray mix which, when applied at a rate of 20 gpa, would deliver to the field 0.10 and 0.20 lb/acre of isopropylamine salt of the active ingredient. Additional spray mixes were made up accordingly containing the glyphosate in descending order of concentration as set forth above together with nonanoic acid at the concentration set forth above, thus providing a series of dilutions of compositions containing both types of active ingredients in combination.

The spray mixes, along with the appropriate checks, were applied to the plants with 3 replication of each treatment. The herbicidal effects 14 DAT were determined as described in Example 1 and are recorded in Table 7.

TABLE 7

| Nonanoic acid lb/acre | Glyphosate lb/acre | Approx. wt. ratio, nonanoic acid to glyphosate | Expected % control | Actual % control | Percent increase over Expected Control |
|---|---|---|---|---|---|
| 0.975 | — | — | — | 0 | — |
| 1.95 | — | — | — | 0 | — |
| 3.90 | — | — | — | 0 | — |
| — | 0.10 | — | — | 60 | — |
| 0.975 | 0.10 | 9.75:1 | 60 | 78 | 30 |
| 1.95 | 0.10 | 19.5:1 | 60 | 85 | 42 |
| 3.90 | 0.10 | 39.0:1 | 60 | 94 | 57 |

EXAMPLE 6

A field trial showing the effect of a mixture of nonanoic acid and glyphosate on control of quackgrass and vetch was performed. The field grown quackgrass and vetch were at 9 and 8 inches tall, respectively, at the time of application. Nonanoic acid spray solutions were prepared as described previously to yield solutions which, when applied at a rate of 30 gpa, would deliver to the field 1.95, 4.90, 5.85, and 7.80 lb/acre of the active ingredient. Glyphosate spray solutions were prepared as in Example 5 from the LAWN AND GARDEN (1.6L) formulation to yield spray solutions which, when applied at a rate of 30 gpa, would deliver to the field 0.125, 0.25, and 0.50 lb/acre of the isopropylamine salt of the active ingredient. Additional spray mixes were made up accordingly containing the glyphosate in descending order concentration as set forth above together with nonanoic acid at the concentration set forth above, thus providing a series of dilutions of compositions containing both types of active ingredients in combination.

The spray mixtures were applied to field plots of approximately 80 square feet total area and each treatment was replicated 3 times. The herbicidal effects of the mixtures 20 DAT on vetch: measured as described in Example 1, are recorded in Table 8. The herbicidal .effect of the mixture at one combination of rates on quackgrass at times from 5–34 DAT are recorded in Table 9.

TABLE 8

| Nonanoic acid lb/acre | Glyphosate lb/acre | Approx. wt. ratio, nonanoic acid to glyphosate | Control of Vetch 20 DAT | | Percent increase over Expected Control |
|---|---|---|---|---|---|
| | | | Expected % control | Actual % control | |
| 1.95 | — | — | — | 2 | — |
| 3.90 | — | — | — | 7 | — |
| 5.85 | — | — | — | 25 | — |
| 7.80 | — | — | — | 30 | — |
| — | 0.125 | — | — | 10 | — |
| — | 0.25 | — | — | 35 | — |
| — | 0.50 | — | — | 47 | — |
| 1.95 | 0.125 | 15.6:1 | 12 | 13 | 10 |
| 3.90 | 0.125 | 31.2:1 | 16 | 32 | 96 |
| 5.85 | 0.125 | 46.8:1 | 33 | 73 | 125 |
| 7.80 | 0.125 | 62.4:1 | 37 | 83 | 124 |
| 1.95 | 0.25 | 7.8:1 | 36 | 32 | neg. |
| 3.90 | 0.25 | 15.6:1 | 40 | 58 | 47 |
| 5.85 | 0.25 | 23.4:1 | 51 | 80 | 56 |
| 7.80 | 0.25 | 31.2:1 | 55 | 80 | 47 |
| 1.95 | 0.50 | 3.9:1 | 48 | 72 | 50 |
| 3.90 | 0.50 | 7.8:1 | 51 | 77 | 52 |
| 5.85 | 0.50 | 11.7:1 | 60 | 83 | 38 |
| 7.80 | 0.50 | 15.6:1 | 63 | 92 | 46 | atoms, or a salt thereof, and a second ingredient which is a chemical herbicide, wherein said chemical herbicide is bentazon.

2. The composition, according to claim 1, wherein said first ingredient can be represented by the following formula:

$$R_1 Y_1 Y_2 COOR_2$$

wherein $R_1$=C6 to C19 saturated or unsaturated hydrocarbon, or an epoxide, or cyclopropane thereof $Y_1$=H, C1–C5 hydrocarbon, or hydroxyl at any position along $R_1$ $Y_2$=H, C1–C5 hydrocarbon, or hydroxyl at any position along $R_1$ $R_2$=H, or salt.

3. The composition, according to claim 1, wherein said first entity has from about seven to about eleven carbons.

4. The composition, according to claim 1, wherein said first entity is unsubstituted.

5. The composition, according to claim 1, wherein said first entity is saturated.

TABLE 9

| | | | Control of Quackgrass a Field Trial Days after treatment | | | | | | | | |
|---|---|---|---|---|---|---|---|---|---|---|---|
| | | | 5 | | | 20 | | | 34 | | |
| Nonanoic lb/acre | Glyphosate lb/acre | Approx. wt. ratio, Nonanoic acid to Glyphosate | Expected Control % | Actual Control % | Percent Increase over Expected Control | Expected Control % | Actual Control % | Percent Increase over Expected Control | Expected Control % | Actual Control % | Percent Increase over Expected Control |
| 7.80 | — | — | — | 17 | — | — | 20 | — | — | 0 | — |
| — | 0.125 | — | — | 0 | — | — | 10 | — | — | 13 | — |
| — | 0.25 | — | — | 0 | — | — | 33 | — | — | 60 | — |
| — | 0.50 | — | — | 0 | — | — | 87 | — | — | 77 | — |
| 7.80 | 0.125 | 62.4:1 | 17 | 38 | 124 | 28 | 82 | 193 | 13 | 57 | 338 |
| 7.80 | 0.25 | 31.2:1 | 17 | 27 | 59 | 46 | 85 | 83 | 60 | 78 | 30 |
| 7.80 | 0.50 | 15.6:1 | 17 | 35 | 100 | 90 | 93 | 4 | 77 | 90 | 17 |

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. An agricultural composition for controlling weeds, said composition comprising a first ingredient which is a monocarboxylic acid having about seven to about twenty carbon atoms, or a salt thereof, and a second ingredient which is a chemical herbicide, wherein said chemical herbicide is bentazon.

6. The composition, according to claim 1, wherein said first entity is decanoic or nonanoic acid.

7. The composition, according to claim 1, wherein said first entity is nonanoic acid.

8. A method for the control of unwanted vegetation, said method comprising the administration to said vegetation of an effective mount of a composition comprising a first ingredient which is a monocarboxylic acid having about seven to about twenty carbons, or a salt thereof, and a second ingredient which is a chemical herbicide, wherein said chemical herbicide is bentazon.

9. The method, according to claim 8, wherein said first ingredient can be represented by the following formula:

$R_1Y_1Y_2COOR_2$ wherein $R_1$=C6 to C19 saturated or unsaturated hydrocarbon, or an epoxide, or cyclopropane thereof $Y_1$=H, C1–C5 hydrocarbon, or hydroxyl at any position along $R_1$ $Y_2$=H, C1–C5 hydrocarbon, or hydroxyl at any position along $R_1$ $R_2$=H, or salt.

10. The method, according to claim 8, wherein said first entity has from about seven to about eleven carbons.

11. The method, according to claim 8, wherein said first entity is decanoic or nonanoic acid.

12. The method, according to claim 8, wherein said first entity is nonanoic acid.

13. A method for the control of unwanted vegetation, said method comprising the sequential application to unwanted vegetation a first composition comprising a monocarboxylic acid having about seven to about twenty carbon atoms, or a salt thereof, and a second composition comprising a chemical herbicide, wherein said chemical herbicide is bentazon.

14. The method, according to claim 13, wherein said monocarboxylic acid can be represented by the following formula:

$R_1Y_1Y_2COOR_2$ wherein $R_1$=C6 to C19 saturated or unsaturated hydrocarbon, or an epoxide, or cyclopropane thereof $Y_1$=H, C1–C5 hydrocarbon, or hydroxyl at any position along $R_1$ $Y_2$=H, C1–C5 hydrocarbon, or hydroxyl at any position along $R_1$ $R_2$=H, or salt.

15. The method, according to claim 13, wherein said monocarboxylic acid is nonanoic acid.

16. The composition, according to claim 1, wherein said first ingredient is nonanoic acid, or a salt thereof, and said chemical herbicide is bentazon.

17. The method, according to claim 8, wherein said first ingredient is nonanoic acid, or a salt thereof, and said chemical herbicide is bentazon.

* * * * *

UNITED STATES PATENT AND TRADEMARK OFFICE
CERTIFICATE OF CORRECTION

PATENT NO. : 5,703,013

DATED : December 30, 1997

INVENTOR(S) : Caulder, et. al.

It is certified that error appears in the above-identified patent and that said Letters Patent is hereby corrected as shown below:

Column 3, line 1: "The specie herbicides" should read --The specific herbicides--;

line 6: should read --Chemical Herbicide Families and Examples--;

line 12: "(acdis, esters)" should read --(acids, esters)--; and line 25: should read --Other Chemical Herbicides --.

Column 4, line 5: "soft-less" should read --soil-less--.

Cols 5&6, Tab. 2, sub-heading, Cols. 6&9: "Percent Increase over Control %" should read --Percent Increase over Expected Control--;

Tab. 2, Col. 5, line 1: "0" should read --1--; and

Tab. 2, Col. 6, line 6: "83" should read --84--.

Cols 7&8, Tab. 3, Sub-heading Cols 6&9: "Percent Increase over Control %" should read --Percent Increase over Expected Control--; and Tab. 4, Sub-heading Cols 6&9: "Percent Increase over Control %" should read --Percent Increase over Expected Control--.

UNITED STATES PATENT AND TRADEMARK OFFICE
CERTIFICATE OF CORRECTION

PATENT NO. : 5,703,013
DATED : December 30, 1997
INVENTOR(S) : Caulder, et. al.

It is certified that error appears in the above-identified patent and that said Letters Patent is hereby corrected as shown below:

Cols 9&10, Tab. 5, Sub-heading Cols 6&9: "Percent Increase over Control %" should read --Percent Increase over Expected Control--.

Column 11, line 7: "vetch:" should read --vetch,--; and line 8: ".effect" should read --effect--.

Signed and Sealed this

Seventh Day of April, 1998

Attest:

BRUCE LEHMAN

Attesting Officer

Commissioner of Patents and Trademarks